United States Patent [19]

Sjönell

[11] Patent Number: 4,871,359
[45] Date of Patent: Oct. 3, 1989

[54] ADAPTER FOR DROP UNIT

[75] Inventor: Göran Sjönell, Lidingö, Sweden

[73] Assignee: Presidentia Medical AB, Stockholm, Sweden

[21] Appl. No.: 4,156

[22] Filed: Jan. 30, 1987

[51] Int. Cl.$^4$ .............................................. A61M 5/14
[52] U.S. Cl. .................................. 604/411; 604/405; 222/81
[58] Field of Search ............... 604/411, 405, 412–414, 604/246, 251, 257; 222/81, 85

[56] References Cited

U.S. PATENT DOCUMENTS

| 1,479,451 | 1/1924 | Buckstein | 604/246 |
| 2,007,449 | 7/1935 | Kernodle et al. | 222/478 |
| 2,196,323 | 4/1940 | Norton et al. | 604/405 |
| 2,362,523 | 11/1944 | Armstrong, Jr. et al. | 222/181 |
| 2,777,443 | 1/1957 | Thomas et al. | 604/411 |
| 3,993,066 | 11/1976 | Virag | 604/246 |
| 4,046,276 | 9/1977 | Winchell et al. | 604/257 |
| 4,473,094 | 9/1984 | Harris | 604/411 |
| 4,675,020 | 6/1987 | McPhee | 604/411 |

FOREIGN PATENT DOCUMENTS

| 1188268 | 6/1985 | Canada . | |
| 1105424 | 3/1960 | France | 604/251 |
| 446713 | 3/1949 | Italy | 604/257 |
| 426896 | 4/1935 | United Kingdom | 222/81 |

Primary Examiner—Dalton L. Truluck
Attorney, Agent, or Firm—Sherman and Shalloway

[57] ABSTRACT

The present invention relates to an improved adapter for a disposal package. The inventive adapter includes a first through hole, extending and terminating in a cylindrical socket, a second through hole provided to receive an aeration tube and a third through hole which opens into a tube socket designed to receive a transparent tube. The transparent tube is designed to be curved around to face toward the bottom of the package to indicate liquid level therein. The adapter is further provided with a cutting means formed in the shape of a triangular pyramid body having edges which form walls terminating in a tip. The base of the cutting edges is spaced a predetermined distance from a face of the adapter to provide a space therebetween thicker than the thickness of the package top to allow package top materials to enter into the space and form a seal. Before the adapter is installed, the aeration tube thereof is in a position reciprocated outwardly from the adapter with respect to its installed position and is covered with a stocking, with the open end of the tube being covered by an air and liquid tight cap.

3 Claims, 4 Drawing Sheets

ADAPTER FOR DROP UNIT

BACKGROUND OF THE INVENTION

This invention relates to an adapter for a drop unit including a chamber, application hose, clip and probe for enteral nutrition. The artificial supply, for example, of nutrients usually is carried out by means of drop, enteral nutrition or parenteral nutrition. The package, usually a flask, containing the nutrient is suspended upsidedown, and the nutrient is supplied via a drop unit either intravenously or via a probe directly to the stomach. When the nutrient is supplied from a flask, the visual observation of the filling degree of the flask does not involve problems.

For economic as well as hygienic reasons, disposal packages holding the nutrient are now being used to an increasing extent, which packages are intended for direct use at the application occasion. In view of varying storage times and of the necessity of protecting the contents in the package against exposure to light for a longer period, the disposable package must be capable of preventing light from contacting the contents, which means that the packing material must bar the light and, consequently, be non-transparent. For safety reasons that package is not emptied without the medical staff knowing about it, and it is a fact based on experience that such disposal packages are exchanged with an ample time margin. This implies waste, which in view of the high costs of the packages and their contents involves for the health service at large very great economic losses.

The conventional can packages, therefore, have not come into use to a large extent, but still flasks are used, in spite of the requirement of limited storage time and of higher costs. However attempts have been made to solve these problems and the Canadian Patent 1 188 268 deals with an adapter to be used in combination with can packages. This adapter is associated with several drawbacks, for instance leaking problems and contamination problems.

SUMMARY OF THE INVENTION

The present invention as it is defined in the characterizing clauses of the claims, has the object to render it possible to use disposal packages in the form of cans a.o. for parenteral and enteral nutrition, solving said problems.

After line 40, kindly add the following paragraph: The inventive adapter includes a first through hole, extending and terminating in a cylindrical socket, a second through hole provided to receive an aeration tube and a third through hole which opens into a tube socket designed to receive a transparent tube. The transparent tube is designed to be curved around to face toward the bottom of the package to indicate liquid level therein.

The adapter is further provided with a cutting means formed in the shape of a triangular pyramid body having edges which form walls terminating in a tip. The base of the cutting edges is spaced a predetermined distance from a face of the adapter to provide a space therebetween thicker than the thickness of the package top to allow package top materials to enter into the space and form a seal.

Before the adapter is installed, the aeration tube thereof is in a position reciprocated outwardly from the adapter with respect to its installed position and is covered with a stocking, with the open end of the tube being covered by an air and liquid tight cap.

BRIEF DESCRIPTION OF THE DRAWINGS

The invention is described in greater detail in the following, with reference to the accompanying drawings, in which.

SPECIFIC DESCRIPTION OF THE PREFERRED EMBODIMENTS

Figure 1:
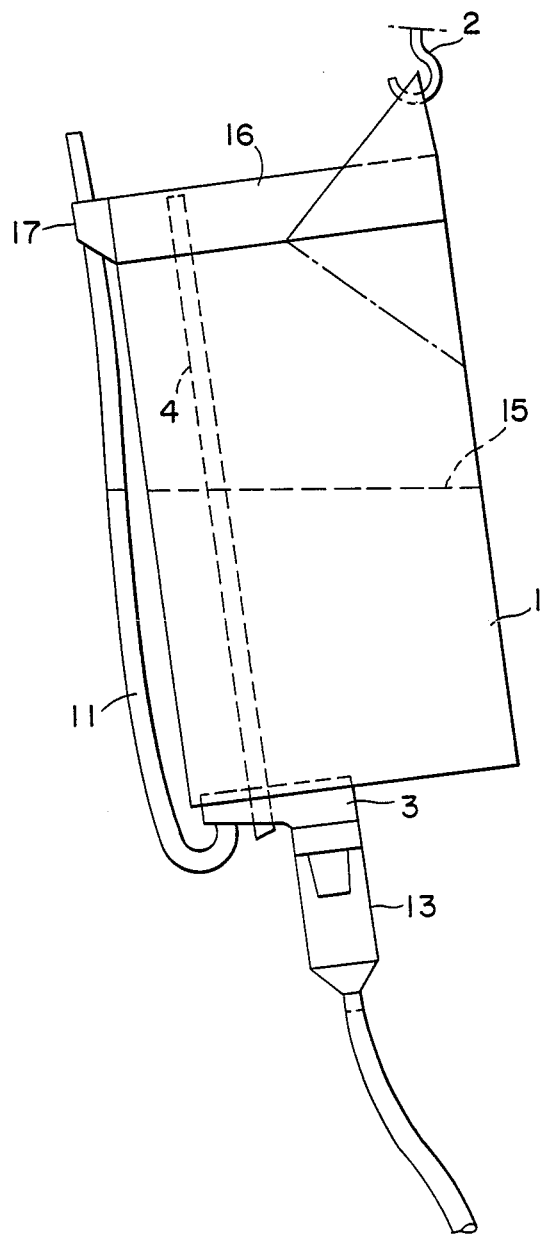
FIG. 1 shows a known adapter applied to a disposal package in the form of a can.

The disposal package in the form of a sheet metal can is designated by 1. The can 1 is shown suspended in a suitable way, for example by means of a hook 2. A member 3 in the form of a plug or an adapter is attached to the can 1. From said plug 3 an aeration tube 4 extends all the way to the vicinity of the can bottom and connects the can interior to the atmosphere.

Figure 2:
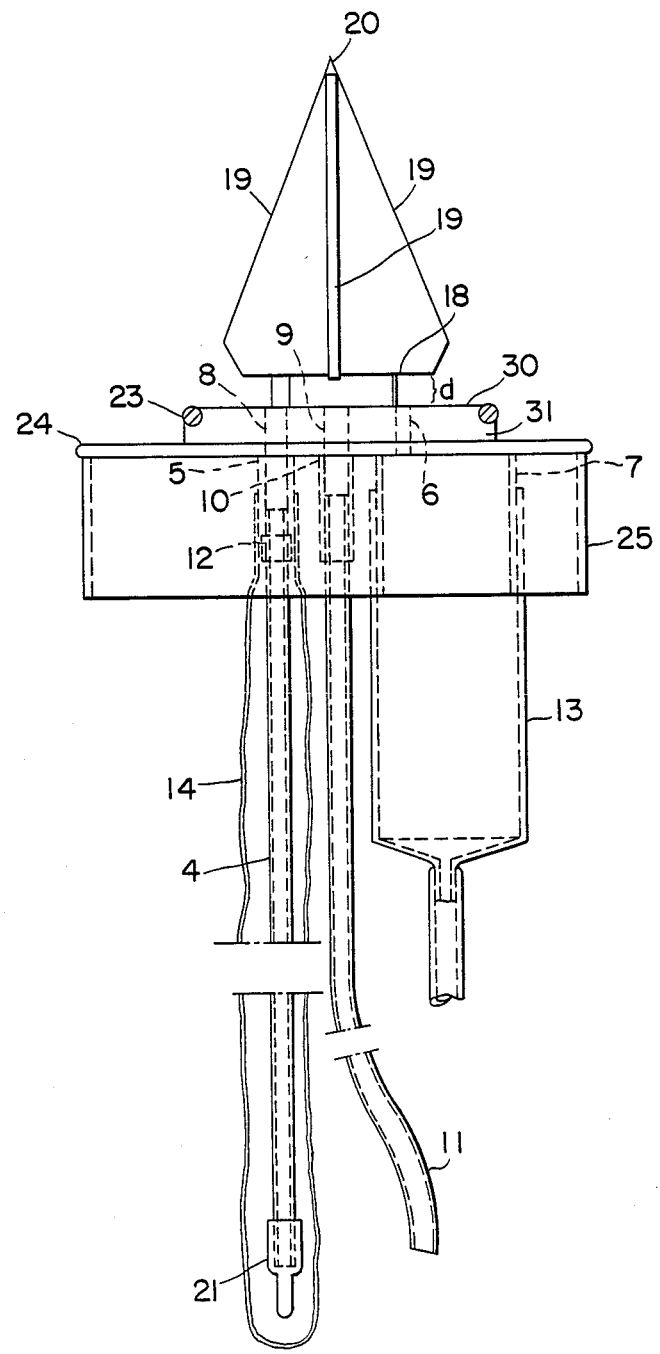
FIG. 2 shows a view of the invented adapter provided with means for penetrating the packing material.
Figure 3:
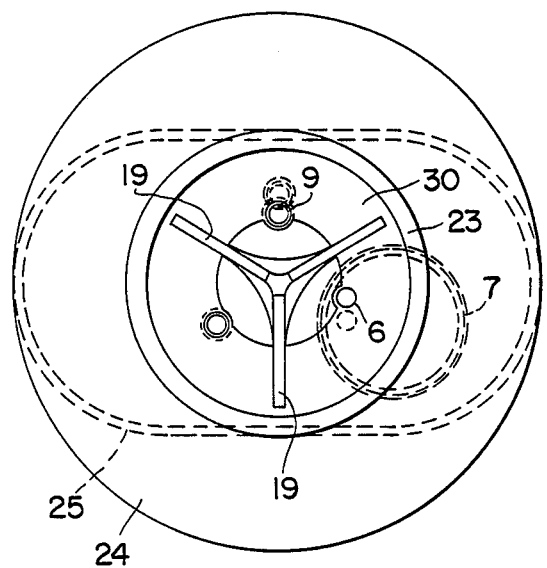
FIG. 3 shows a view from above of this embodiment and FIG. 4 shows the adapter having penetrated a can.
Figure 4:
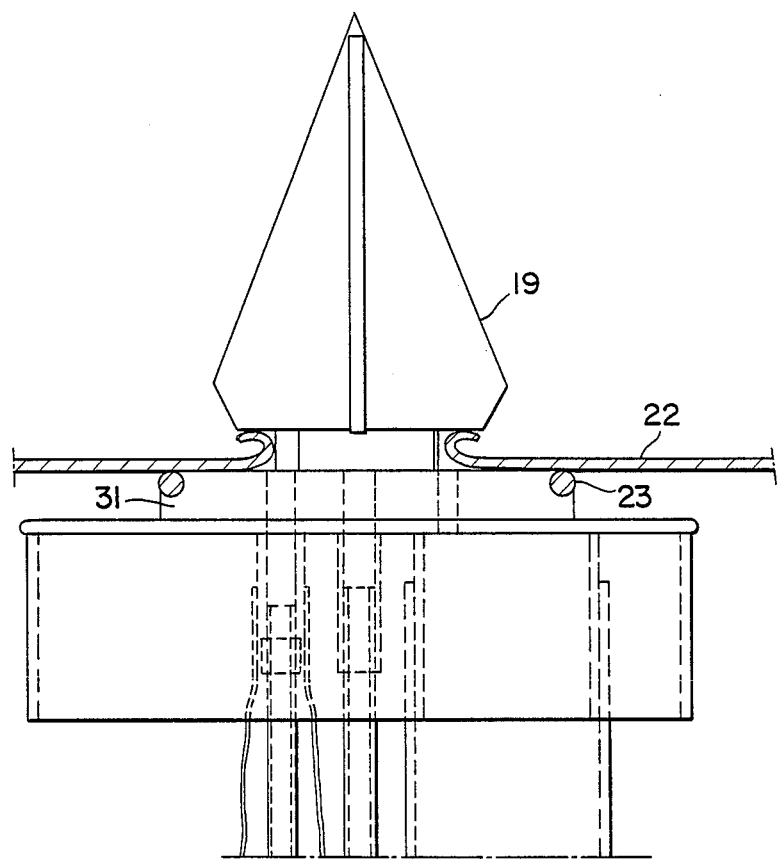

FIG. 2 is a view of the adapter according to the invention. From the side of the member facing to the can interior, a first through hole 6 extends and terminates in a cylindrical socket 7. A second through hole 8 is provided to receive the aforesaid aeration tube 4. The adapter further is provided with a third through hole 9, which opens into a tube socket 10 formed in the member. To said socket 10 a tube or hose 11 is to be connected, as will be described below. The hole 8 also opens into a tube socket 5, the outer end of which is provided with a gasket 12, in which the aeration tube 4 sealingly is displaceable. Fitted to the tube socket 5 is a stocking 14 or the like, which surrounds the tube 4, preventing it from being contaminated before use, when the tube 4 is arranged as shown in FIG. 2 with its inner end withdrawn from the face 30 of a shoulder 31.

The chamber 13 shown, in conventional manner included in the drop unit, is intended to be attached with press fit on the cylindrical socket 7. The drop unit further according to a known standard comprises application hose, clip and probe (not shown).

The transparent tube or hose 11 is intended to be held extending along the outer surface of the can, whereby the liquid level 15 in question in the package easily can be observed in the tube 11. For correctly supporting the tube 11, the package is provided with a retainer 16 about the can bottom, which retainer includes a slit or aperture 17 holding the tube in the position shown in FIG. 1.

The adapter is further provided with a cutting means known per se in the form of a triangular pyramid body, the edges 19 of which form walls terminating in a tip 20. The body can be manufactured of hard plastic, while the tip 20 is of metal. The base 18 of the cutting edges 19 extends with a distance d from the face 30 of the shoulder 31 to form a space. This distance d of the space is greater than the thickness of the sheet metal thickness of the can 1 in the place where the adapter is to be attached. When the cutting means 19 are penetrating the sheet metal 22 this is bending or deflecting aside as the adapter is moved inwardly and finally slightly turned.

The adapter member 3 further is provided with a gasket 23. In the case referred to, the adapter proper is used to make a hole in the can material, in that the cutting edge of the adapter with the edges 19 is pressed through the can material 22 until the adapter member with the gasket 23 abuts the same. The adapter thereafter is slightly turned as mentioned, so that the can material engages beneath the base 18 of the cutting edges. The deflected material of the sheet metal 22 acts as a spring and firmly presses the adapter and its gasket 23 sealingly against the can bottom. The aeration tube 4 is displaced in the opening 8 and the gasket 12, and the stocking 14 is removed when the tube 4 is installed as shown in FIG. 1. According to the invention the aeration tube 4 is provided with an air and liquid tight cap 21. When the tube 4 is displaced into the can 1 and the liquid, a cushion of air is building up in the tube and with the tube in place in the can and its inner end above the liquid level 15 the cap 21 could be removed without any leakage of content through tube 4. The adapter is now ready for use.

The adapter is further provided with a flat, circular plate or disk 24 to which an elliptical flange 25 or the like is provided, preferably in one piece with the disk. These parts 24 and 25 surround and protect the sockets 7, 5, 10 and at the same time the flange 25 forms a handle, facilitating the manipulation of the adapter.

The adapter according to the invention, of course, can be designed in different ways within the scope of the invention. The position of the holes in the member, for example, can be varied relative to each other, and is it clear from the figures that the locations of the holes 6, 8 and 9 and corresponding recesses, made in the shoulder 31, are such that the can material 22 does not interfere or block the holes when penetrated by the adapter cutting means.

I claim:

1. An adapter for a disposal package having a bottom and a top, said adapter comprises a main member intended to sealingly be attached to the package, which package in use occupies a position with the adapter positioned in the bottom, which main member is provided with a first through hole for emptying the contents of the package, a second through hole for an aeration tube, a third through hole for a transparent tube, that the main member is provided with cutting means of pyramid shape to penetrate the package material, said cutting means having a base provided with a space for receiving between said cutting means and the main member the package material to thereby lock the member to the package when the main member and therewith the cutting means are turned, characterized in that the aeration tube before the use is extended outside the adapter with its end, intended to be placed in the package and above the liquid level, withdrawn into the second hole, that a stocking is fitted to the second hole and surrounds the extended aeration tube, that the other end of the tube is provided with an air and liquid tight separate cap removable from the end, said cap being replaceably separable from said tube other end, that the second hole is provided with a gasket sealingly engaging the displaceable aeration tube, and that the space makes a distance between the base of the cutting means and the main member which is greater that the thickness of the package material.

2. An adapter as defined in claim 1, characterized in that the mainbody is forming a plate or disk provided with a perpendicular, substantially elliptic flange, making a handle.

3. An adapter as defined in claim 2, characterized in that the flange surrounds the connections of tubes to the first, second and third through holes respectively, formning a protection.

* * * * *